(12) United States Patent
Hartley

(10) Patent No.: US 7,294,147 B2
(45) Date of Patent: Nov. 13, 2007

(54) COMPOSITE PROSTHESIS

(75) Inventor: David Ernest Hartley, Subiaco (AU)

(73) Assignees: Cook Incorporated, Bloomington, IN (US); William Cook Europe ApS, Bjaeverskov (DK); William A. Cook Australia Pty. Ltd., Brisbane (AU)

( * ) Notice: Subject to any disclaimer, the term of this patent is extended or adjusted under 35 U.S.C. 154(b) by 749 days.

(21) Appl. No.: 10/645,095

(22) Filed: Aug. 21, 2003

(65) Prior Publication Data

US 2004/0082990 A1 Apr. 29, 2004

Related U.S. Application Data

(60) Provisional application No. 60/405,769, filed on Aug. 23, 2002.

(51) Int. Cl.
*A61F 2/06* (2006.01)

(52) U.S. Cl. .................... 623/1.13; 623/1.35

(58) Field of Classification Search .......... 623/1.35, 623/1.13, 1.16, 1.15, 1.3, 1.31, 1.11; 606/191, 606/195, 198
See application file for complete search history.

(56) References Cited

U.S. PATENT DOCUMENTS

| | | | |
|---|---|---|---|
| 5,387,235 A | 2/1995 | Chuter | |
| 5,720,776 A | 2/1998 | Chuter et al. | |
| 5,916,263 A | 6/1999 | Goicoechea et al. | |
| 6,206,931 B1 | 3/2001 | Cook et al. | |
| 6,325,823 B1 | 12/2001 | Horzewski et al. | |
| 6,409,756 B1 | 6/2002 | Murphy | |
| 6,524,336 B1 * | 2/2003 | Papazolgou et al. | ....... 623/1.35 |
| 6,939,370 B2 | 9/2005 | Hartley et al. | |
| 7,160,318 B2 * | 1/2007 | Greenberg et al. | ......... 623/1.13 |
| 2003/0120332 A1 | 6/2003 | Hartley | |
| 2003/0233140 A1 | 12/2003 | Hartley et al. | |
| 2004/0054396 A1 | 3/2004 | Hartley et al. | |
| 2004/0106978 A1 | 6/2004 | Greenberg et al. | |
| 2004/0256759 A1 | 12/2004 | Hartley | |

FOREIGN PATENT DOCUMENTS

| | | |
|---|---|---|
| WO | WO 98/53761 | 12/1998 |
| WO | WO 99/29262 | 6/1999 |
| WO | WO 03/034948 | 5/2003 |

* cited by examiner

*Primary Examiner*—Kevin T. Truong
(74) *Attorney, Agent, or Firm*—Richard J. Godlewski

(57) ABSTRACT

A prosthesis assembly for deployment in an aorta to span an aortic aneurysm. The prosthesis assembly has at least first and second members (2,4) with an end portion (12) of one member (2) to be joined to an end portion (24) of the other member (4) when in and when expanded within a lumen of a patient. Each member (2,4) has a stent arrangement (10,25) associated with a graft arrangement (8,26). The end portion of one member has at least part of its stent arrangement on the inner surface of its graft arrangement and the end portion of the other member has at least part of its stent arrangement on the inner surface of its graft arrangement. Advantageously two stents are overlapped. The joining portions of the first and second members can have the same diameter.

6 Claims, 4 Drawing Sheets

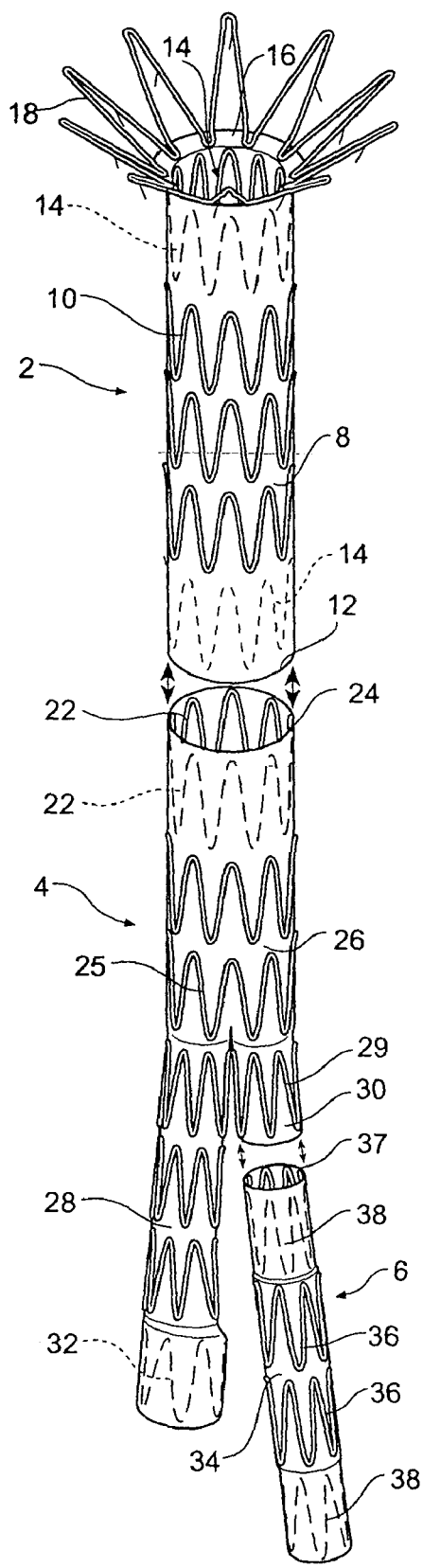
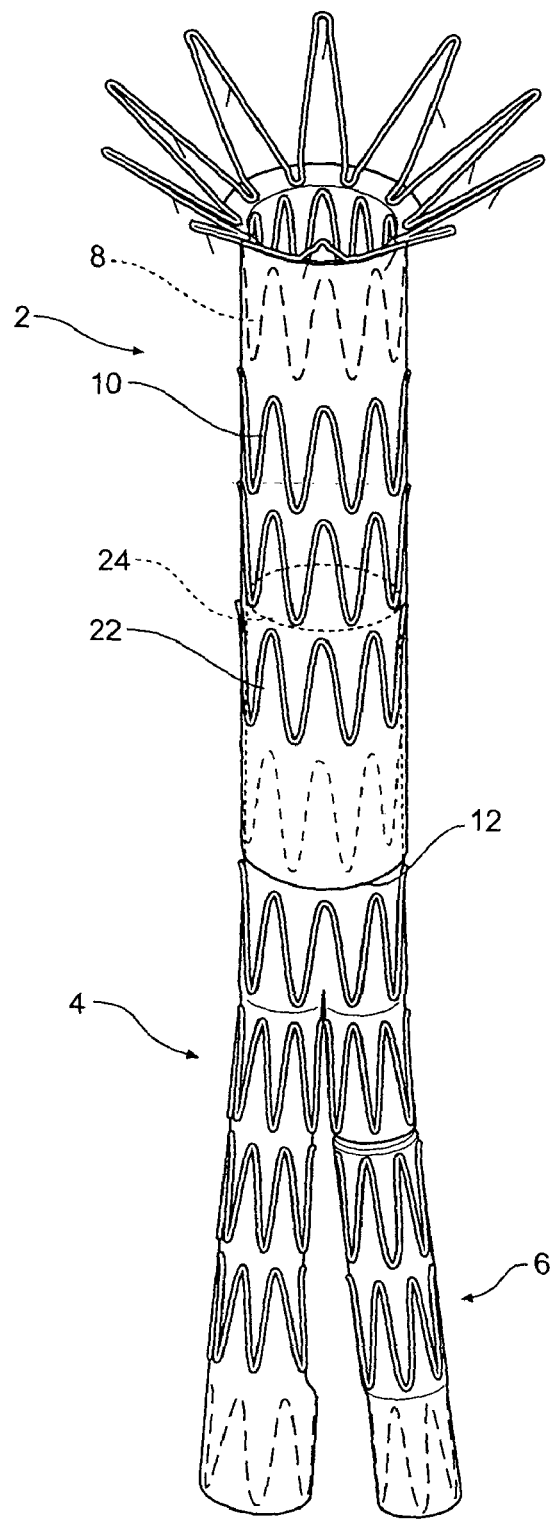
Fig 1
Fig 2

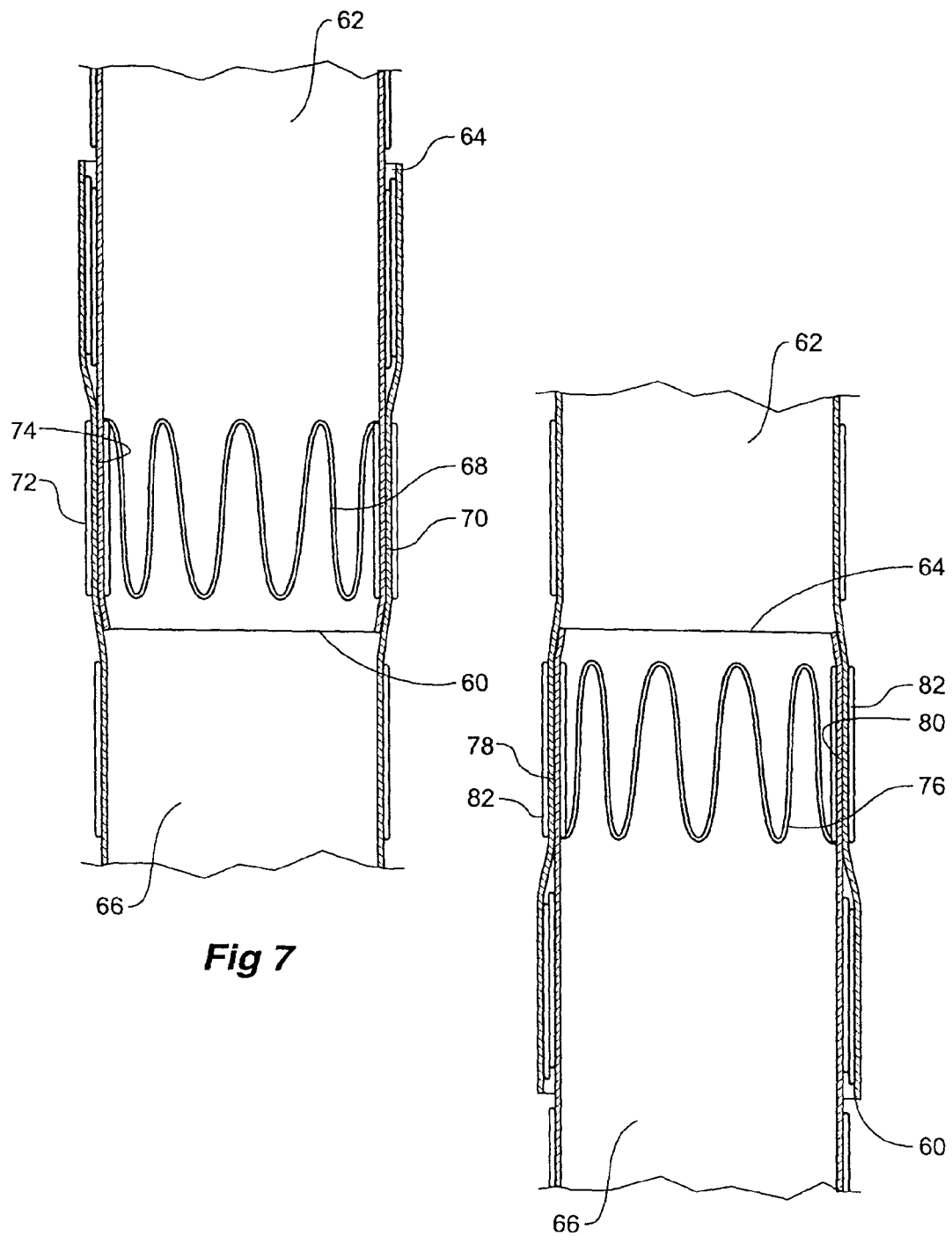

COMPOSITE PROSTHESIS

CROSS-REFERENCE TO RELATED APPLICATIONS

This application claims priority of provisional application Ser. No. 60/405,769, filed Aug. 23, 2002.

TECHNICAL FIELD

This invention relates to prosthesis for implantation within the human or animal body for the repair of damaged lumens such as blood vessels.

BACKGROUND OF THE INVENTION

Although this invention will be discussed with respect to its application to repair of abdominal aortic aneurysms the invention is not so limited and may apply to prosthesis for repair of other lumens within the human or animal body.

Throughout this specification when discussing the application of this invention to the aorta the term distal with respect to a prosthesis is intended to refer to the end of the prosthesis furthest away in the direction of blood flow from the heart and the term proximal is intended to mean the end of the prosthesis which when implanted would be nearest to the heart.

In our earlier patent specification published number WO98/53761 an endoluminal prosthesis was disclosed which in particular was useful for repair of aortic aneurysms. A problem with such a prosthesis is that for different persons or animals different size prostheses must be constructed because the specific dimensions of an aorta are quite variable in each of length, diameter and angulation between the renal artery region and the region of the aortic bifurcation.

SUMMARY OF THE INVENTION

It is the object of this invention to provide a composite prosthesis which can be assembled to fit a range of lengths of aorta thereby saving inventory costs and enabling off the shelf supply of a prosthesis assembly.

In one form therefore although this may not necessarily be the only or broadest form the invention is said to reside in a prostheses assembly adapted for deployment in an aorta to span an aortic aneurysm, comprising at least first and second members with an end portion of one member to be joined to an end portion of the other member portion when in and when expanded within a lumen of a patient, wherein each member comprises a stent arrangement associated with a graft arrangement, wherein the end portion of one member has at least part of its stent arrangement on the inner surface of its graft, and wherein the end portion of the said other member has at least part of its stent arrangement on the inner surface of its graft.

In an alternative form the invention is said to reside in a two part stent graft prostheses assembly comprising at least first and second members to be located within and joined together within a lumen of a patient, wherein one member is to be initially located and expanded within the lumen, said one member having one end portion with one or more stents on the inner surface of the graft, wherein the other member is to be sequentially located within and expanded within the said lumen and has a second end portion to be located within the said one end portion, and wherein the said second end portion has a graft portion with a stent or stents on the inside surface thereof, so that when the said one and said other end portions are in engagement with one another there is no stent material between the engaging portions.

Preferably the said one member has a stent or stents on the outer surface of a further part or the remainder of the graft of the said one member and the said other member has a stent or stents on the outer surface of a further part or the remainder of the graft of the said other member.

Preferably the stent graft prosthesis member for use with the above assembly of claim comprises a stent or stents on one graft surface at one end portion thereof, and further comprises a stent or stents on at least a part of the other graft surface which part is spaced longitudinally from the said one end portion.

In an alternative form the invention is said to reside in a composite prosthesis adapted for deployment in a lumen, the prosthesis comprising a first substantially tubular prosthesis portion and a second substantially tubular prosthesis portion, characterized by each prosthesis portion having a plurality of self expanding stents on an outer surface thereof along the length of each portion and at least one self expanding stent on an inside surface thereof at each end of each portion, each prosthesis portion having a connecting end adapted to engage with the connecting end of the other prosthesis portion and a remote end at the opposite end to the connecting end, each connecting end having the same outside diameter as the other connecting end, whereby in use the connecting end of the first prosthesis portion can be deployed either inside or outside the connecting end of the second prosthesis portion with at least two stents overlapping.

In further form the invention is said to reside in a composite prosthesis adapted for deployment in an aorta to span an aortic aneurysm adjacent to or including an aortic bifurcation, the prosthesis comprising a substantially tubular proximal prosthesis portion and a substantially tubular distal prosthesis portion, characterised by each prosthesis portion having a plurality of self expanding stents on an outer surface thereof along the length of each portion and at least one self expanding stent on an inside surface thereof at each end of each portion, each prosthesis portion having a connecting end adapted to engage with the connecting end of the other prosthesis portion and a remote end at the opposite end to the connecting end, each connecting end having the same outside diameter as the other connecting end, whereby in use the connecting end of the proximal prosthesis portion can be deployed either inside or outside the connecting end of the distal prosthesis portion with at least two stents overlapping such that the either the distal or proximal prosthesis portion can be deployed first and the other prosthesis portion deployed so that its connecting end is within the connecting end of the first deployed prosthesis portion.

It will be seen that by these general forms of the invention the amount of overlap of the first and second or proximal and distal prosthesis can be varied thereby enabling a variety of lengths of aorta or other body lumen or the region being spanned in the aorta to be allowed for. The ability to deploy with the connecting end either inside or outside means that the either the first or second prosthesis portion can be deployed first and then the other one deployed inside it. This gives a physician considerable flexibility and means that a hospital can have a stock of prostheses which can be readily assembled depending upon the observed vasculature.

Having the same diameter for each connecting end means that an interference fit is obtained whether one connecting end goes inside or outside the other connecting end.

In one form of the invention the second or distal prosthesis portion may be a bifurcated graft having a body portion and two leg portions. Alternatively the second or distal prosthesis portion may be an aorto-uni-iliac prosthesis.

The bifurcated second or distal prosthesis portion may have a shorter leg and a longer leg and there may be self expanding stents on the outside of the shorter leg and the inside of the distal end of the longer leg.

There may be further included at least one leg prosthesis portion. The leg prosthesis portion may be adapted to be deployed in to either the longer or shorter legs of the bifurcated second or distal prosthesis portion or into the end of the aorto-uni-iliac prosthesis.

The first or proximal prosthesis portion may be provided with a proximally extending self expanding stent. Such a proximally extending self expanding stent may include barbs to engage against the wall of a lumen to hold the graft in place. This proximally extending self expanding stent may be adapted to span across the renal arteries to provide good mounting of the composite prosthesis within the aorta.

Each of the stents may be zig zag or z-stents made from nitinol or stainless steel.

Where it is desirable for the prosthesis portions to be flexible to allow for angulation of or curves in the aorta the stents along the length of the prosthesis portion may be spaced apart along the graft material. Spacing of stents may be from 0 mm to 8 mm. More flexibility may be provided on the proximal portion than the distal portion.

In an alternative form the stents may be balloon expandable stents.

BRIEF DESCRIPTION OF THE DRAWING

This then generally describes the invention but to assist with understanding reference will now be made to the accompanying drawings which show preferred embodiments of the invention.

FIG. 1 shows a first embodiment of composite prosthesis according to the invention in an exploded view;

FIG. 2 shows an assembled view of the embodiment shown in FIG. 1;

FIG. 7 shows an detailed cut away view of the connecting region of a prosthesis assembly of one embodiment of the invention showing the bottom up approach; and FIG. 8 shows an detailed cut away view of the connecting region of a prosthesis assembly of one embodiment of the invention showing the top down approach.

DETAILED DESCRIPTION

Figures 3, 4:
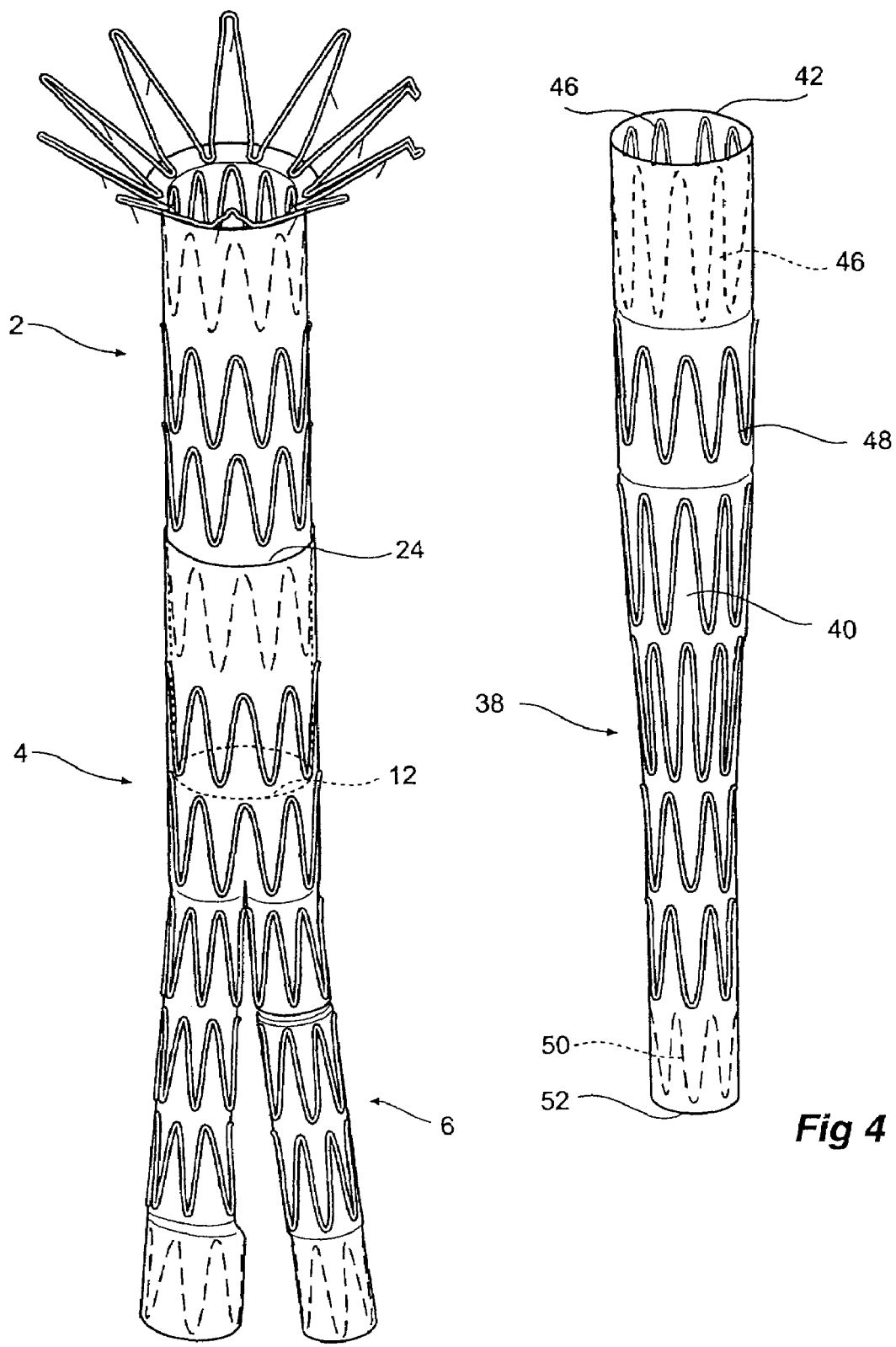
FIG. 3 shows an alternate assembled view of the embodiment shown in FIG. 1.
FIG. 4 shows an alternative embodiment of a distal prosthesis portion according to the invention.

U.S. Pat. No. 5,387,235 entitled "Expandable Transluminal Graft Prosthesis For Repair Of Aneurysm" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Barb and Expandable Transluminal Graft Prosthesis For Repair of Aneurysm" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

PCT Patent Publication No. WO 99/29262 entitled "Endoluminal Aortic Stents" discloses a fenestrated prosthesis for placement where there are intersecting arteries. This feature and other features disclosed in PCT Patent Publication No. WO 99/29262 could be used with the present invention and the disclosure of PCT Patent Publication No. WO 99/29262 is herewith incorporated in its entirety into this specification.

PCT Patent Publication No. WO 03/034948 entitled "Prosthesis For Curved Lumens" discloses prostheses with arrangements for bending the prosthesis for placement into curved lumens. This feature and other features disclosed in PCT Patent Publication No. WO 03/034948 could be used with the present invention and the disclosure of PCT Patent Publication No. WO 03/034948 is herewith incorporated in its entirety into this specification.

U.S. Provisional Patent Application Ser. No. 60/392,682, filed Jun. 28, 2002, and U.S. patent application Ser. No. 10/447,406, filed May 29, 2003, entitled "Trigger Wires" disclose release wire systems for the release of stent grafts retained on introducer devices. This feature and other features disclosed in U.S. Provisional Patent Application Ser. No. 60/392,682 and U.S. patent application Ser. No. 10/447,406, filed May 29, 2003 could be used with the present invention and the disclosure of U.S. Provisional Patent Application Ser. No. 60/392,682 and U.S. patent application Ser. No. 10/447,406, filed May 29, 2003 are herewith incorporated in their entirety into this specification.

U.S. Provisional Patent Application Ser. No. 60/392,667, filed Jun. 28, 2002, and U.S. patent application Ser. No. 10/609,846, filed Jun. 30, 2003, entitled "Thoracic Deployment Device" disclose introducer devices adapted for deployment of stent grafts particularly in the thoracic arch. This feature and other features disclosed in U.S. Provisional Patent Application Ser. No. 60/392,667 and U.S. patent application Ser. No. 10/609,846, filed Jun. 30, 2003 could be used with the present invention and the disclosure of U.S. Provisional Patent Application Ser. No. 60/392,667 and U.S. patent application Ser. No. 10/609,846, filed Jun. 30, 2003 are herewith incorporated in their entirety into this specification.

U.S. Provisional Patent Application Ser. No. 60/392,599, filed Jun. 28, 2002, and U.S. patent application Ser. No. 10/609,835, filed Jun. 30, 2003, entitled "Thoracic Aortic Aneurysm Stent Graft" disclose stent grafts that are useful in treating aortic aneurysms particularly in the thoracic arch. This feature and other features disclosed in U.S. Provisional Patent Application Ser. No 60/392,599 and U.S. patent application Ser. No. 10/609,835, filed Jun. 30, 2003 could be used with the present invention, and the disclosure are herewith incorporated in their entirety into this specification.

U.S. Provisional Patent Application Ser. No. 60/391,737, filed Jun. 26, 2002, entitled "Stent-Graft Fastening Arrangement" discloses arrangements for fastening stents onto grafts particularly for exposed stents. This feature and other features disclosed in U.S. Provisional Patent Application No. 60/391,737 could be used with the present invention and the disclosure of U.S. Provisional Patent Application Ser. No. 60/391,737 is herewith incorporated in its entirety into this specification.

U.S. Provisional Patent Application Ser. No. 60/405,367, filed Aug. 23, 2002, entitled "Asymmetric Stent Graft Attachment" discloses retention arrangements for retaining onto and releasing prostheses from introducer devices. This feature and other features disclosed in U.S. Provisional Patent Application Ser. No. 60/405,367 could be used with the present invention and the disclosure of U.S. Provisional Patent Application Ser. No. 60/405,367 is herewith incorporated in its entirety into this specification.

U.S. patent application Ser. No. 10/322,862, filed Dec. 18, 2002, entitled "Stent Graft With Improved Adhesion" discloses arrangements on stent grafts for enhancing the adhesion of such stent grafts into walls of vessels in which they are deployed. This feature and other features disclosed in U.S. patent application Ser. No. 10/322,862 could be used with the present invention and the disclosure of U.S. patent application Ser. No. 10/322,862 is herewith incorporated in its entirety into this specification.

Now looking more closely to the drawings and in particular the embodiment shown in FIGS. 1, 2 and 3 it will be seen that the composite prosthesis includes a first or proximal prosthesis portion 2, a second or distal prosthesis portion 4 and leg prosthesis portion 6. The first or proximal prosthesis portion 2 comprises a fabric material graft body 8 of substantially tubular form with self expanding zig zag stents 10 on the outside along most of its length and self expanding zig zag stents 14 within the tubular body 8 at the proximal end 16 and distal end 12. Extending from the proximal end 16 is a supra-renal zig zag stent 18 with barbs 20 extending distally to provide fixation into the wall of the aorta.

The zig-zag stents are also well known as Gianturco Z-stents commercially available from William A Cook Australia Pty Ltd, Brisbane, Australia or Cook Inc, Bloomington, Ind., USA. The graft material is typically DACRON® material available from a number of medical graft manufacturers.

The zig zag stent within the proximal end 16 of the first or proximal prosthesis portion 2 assists with sealing of the graft against the walls of the aorta and the external zig zag stents provide a smooth inner surface for the flow of blood through the prosthesis. The internal zig zag stent 14 at the distal end 12 provides an outer surface of the tubular body 8 which is smooth and can seal within the proximal end of the second or distal prosthesis portion 4 when it is deployed within the second or distal prosthesis portion 4.

The second or distal prosthesis portion 4 comprises a fabric material graft body 26 and has an internal zig zag stent 22 at its proximal end 24 so that the outer surface of its tubular body 26 is smooth and can seal within the distal end of the first or proximal prosthesis portion 2 when it is deployed within the first or proximal prosthesis portion 2. The external zig zag stents 25 provide a smooth inner surface for the flow of blood through the prosthesis.

Towards the distal end of the second or distal prosthesis portion 4 the tubular body 26 bifurcates into a longer leg 28 and a shorter leg 30 each of which has zig zag stents 29 on its outside surface except the terminal zig zag stent 32 on the longer leg.

The leg prosthesis portion 6 which is adapted to extend into the contralateral-iliac artery is comprised from a tubular fabric material body 34 with outside zig zag stents 36 along its length except for internal zig zag stents 38 at its proximal and distal ends.

FIG. 2 shows the assembled prosthesis in a first arrangement or configuration in which the connecting end 24 of the second or distal prosthesis portion 4 is deployed within the distal connecting end 12 of the first or proximal prosthesis portion 2. It will be realized that the amount of overlap between the first or proximal prosthesis portion 2 and the second or distal prosthesis portion 4 can be varied for different lengths of an aorta from the renal arteries to the aortic bifurcation. It is preferable, however, that there is at least a longitudinal or axial overlap of two stents. This means that there will be a smooth inner surface of one portion engaged against a smooth outer surface of the other portion to provide a good seal. The leg prosthesis portion 6 is deployed with its proximal end 37 within the shorter leg 30 of the second or distal prosthesis portion 4.

The prosthesis in FIG. 2 is assembled in what is also known as a top down approach or assembly. The physician will deploy the proximal prosthesis portion 2 first in the aorta of a patient followed by deploying or placing the distal prosthesis portion 4 in the aorta with the proximal end 24 of the distal prosthesis portion 4 inside the distal end 12 of the proximal prosthesis portion 2.

FIG. 3 shows the assembled prosthesis in a second arrangement in which the connecting end 12 of the first or proximal prosthesis portion 2 is deployed within the connecting end 24 of the second or distal prosthesis portion 4. It will be realized that the amount of overlap between the first or proximal prosthesis portion 2 and the second or distal prosthesis portion 4 can be varied for different lengths of an aorta from the renal arteries to the aortic bifurcation. It is preferable, however, that there is at least an overlap of two stents. This means that there will be a smooth inner surface of one portion engaged against a smooth outer surface of the other portion to provide a good seal. The leg prosthesis portion 6 is deployed with its proximal end 37 within the shorter leg 30 of the second or distal prosthesis portion 4.

The prosthesis in FIG. 3 is assembled in a second arrangement or configuration in what is also known as a bottom up approach or assembly. Here, the physician deploys the distal prosthesis portion 4 first in the aorta of a patient followed by deploying or placing the proximal prosthesis portion 2 through the distal prosthesis portion 4 and into the aorta with the distal connecting end 12 of the proximal prosthesis portion 2 inside the proximal connecting end 24 of the distal prosthesis portion 4.

Figure 5:
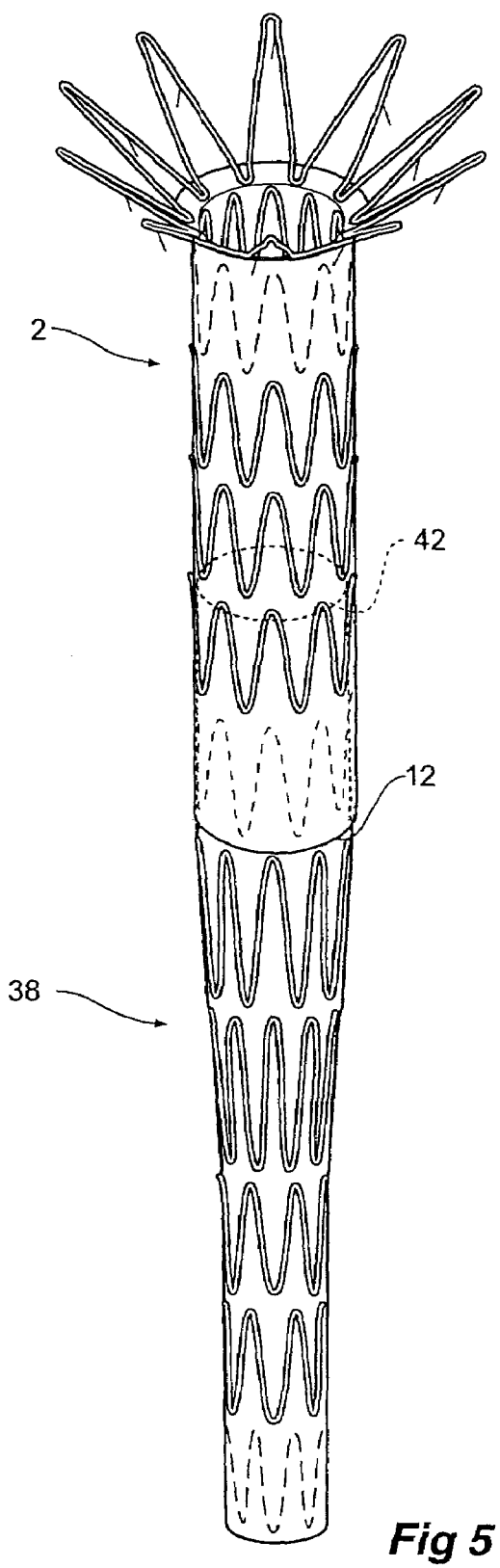
FIG. 5 shows an assembled view of part of the embodiment shown in FIG. 1 and the embodiment shown in FIG. 4.
Figure 6:
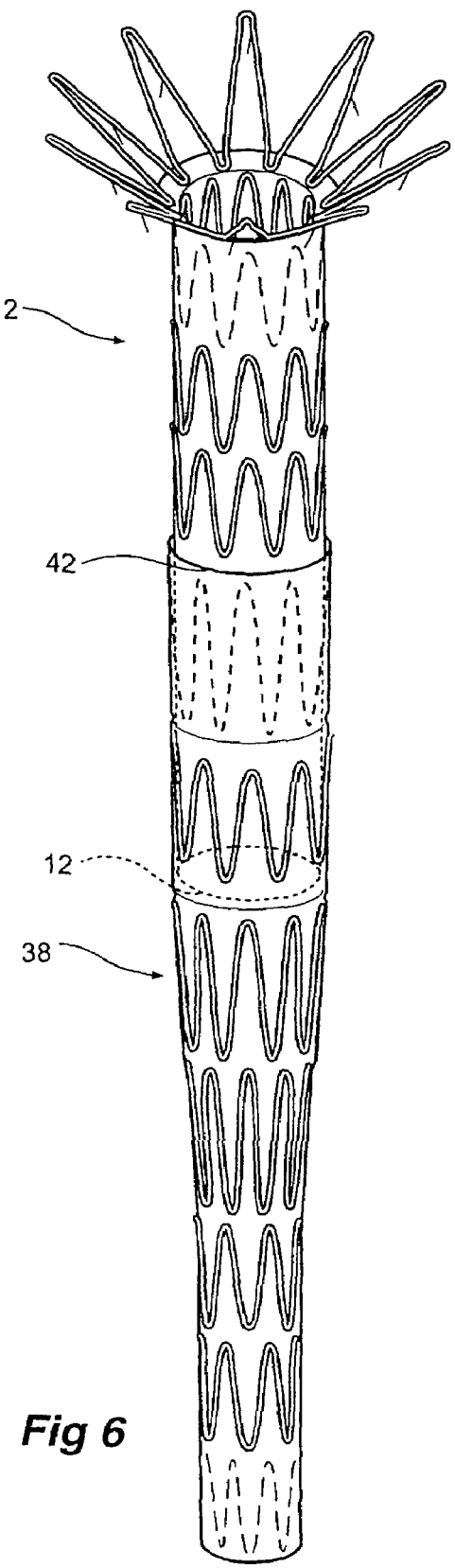
FIG. 6 shows an alternate assembled view of part of the embodiment shown in FIG. 1 and the embodiment shown in FIG. 4.

FIG. 4 shows an aorto-uni-iliac prosthesis portion 38 which is suitable as an alternative second or distal prosthesis portion. This portion 38 is adapted to be deployed inside or outside a first or proximal prosthesis portion as depicted in FIGS. 5 or 6 and to extend from the aorta into either of the iliac arteries. In such a situation a plug would normally be deployed into the other iliac artery.

The aorto-uni-iliac prosthesis portion 38 comprises a tubular slightly tapered body 40 with a proximal end 42 and a distal end 52. The taper is used because the iliac arteries are normally of lesser diameter than the aorta. The aorto-uni-iliac prosthesis portion 38 has an internal zig zag stent 46 at its proximal end 42 so that the outer surface of its tubular body 40 is smooth and can seal within the distal end of the first or proximal prosthesis portion 2 when it is deployed within the first or proximal prosthesis portion 2. The external zig zag stents 48 provide a smooth inner surface for the flow of blood through the prosthesis. The internal zig zag stent 50 at the distal end 52 provides an outer surface of the tubular body 40 which is smooth and can seal within and against the wall of the iliac artery when it is deployed.

FIG. 5 shows an assembled aorto-uni-iliac prosthesis in a first arrangement or configuration in which the connecting end 42 of the aorto-uni-iliac prosthesis portion 38 is deployed within the proximal connecting end 12 of the first or proximal prosthesis portion 2. It will be realised that the amount of overlap between the first or proximal prosthesis portion 2 and the aorto-uni-iliac prosthesis portion 38 can be varied for different lengths of an aorta from the renal arteries to the aortic bifurcation and to a suitable landing spot in one of the iliac arteries. It is preferable, however, that there is at least an overlap of two stents. This means that there will be a smooth inner surface of one portion engaged against a smooth outer surface of the other portion to provide a good seal.

FIG. 6 shows an assembled aorto-uni-iliac prosthesis in a second arrangement or configuration in which the distal connecting end 12 of the first or proximal prosthesis portion 2 is deployed within the connecting end 42 of the aorto-uni-iliac prosthesis portion 38. It will be realised that the amount of overlap between the first or proximal prosthesis portion 2 and the aorto-uni-iliac prosthesis portion 38 can be varied for different lengths of an aorta from the renal arteries to the aortic bifurcation and to a suitable landing spot in one of the iliac arteries. It is preferable, however, that there is at least an overlap of two stents. This means that there will be a smooth inner surface of one portion engaged against a smooth outer surface of the other portion to provide a good seal.

The use of the aorto-uni-iliac prosthesis in either the first or second configuration again depends upon the whether the physician prefers to utilise a top down or bottom up approach or assembly as previously described.

FIG. 7 shows an detailed cut away view of the connecting region of a prosthesis assembly of one embodiment of the invention showing the bottom up approach.

In this embodiment the distal end 60 of the proximal portion 62 is deployed within the proximal end 64 of the distal prosthesis portion 66. The end stent 68 of the proximal portion 62 is inside the graft material of that portion and hence the outer surface 70 in that region is smooth. The end stent but one 72 of the distal prosthesis portion 66 is on the outside of the graft material so that the inner surface 74 in that region is smooth. These smooth surfaces 70 and 74 engage with each other when the prosthesis is assembled and provide a seal between the proximal and distal portions.

FIG. 8 shows an detailed cut away view of the connecting region of a prosthesis assembly of one embodiment of the invention showing the top down approach.

In this embodiment the proximal end 64 of the distal portion 66 is deployed within the distal end 64 of the proximal prosthesis portion 62. The end stent 76 of the distal portion 66 is inside the graft material of that portion and hence the outer surface 78 in that region is smooth. The end stent but one 82 of the proximal prosthesis portion 62 is on the outside of the graft material so that the inner surface 80 in that region is smooth. These smooth surfaces 78 and 80 engage with each other when the prosthesis is assembled and provide a seal between the proximal and distal portions.

Intended Use

In one embodiment the composite prosthesis of the present invention is intended to treat aneurysms of the abdominal aortic or aortoiliac by excluding the aneurysmal portion of that vessel from arterial flow and pressure. The composite is a multi-piece device and is to be used in instances where the implanting physician desires the ability to vary the overall length of the device by 'tromboning' or for applications where an increase in the angulation of the neck is required. The device is inserted via surgical cutdown into a femoral artery, the device is advanced into the desired position over a stiff wire guide using endovascular interventional techniques. A range of endovascular graft lengths and diameters are offered to the implanting physician to cater for individual patient anatomies.

The composite prosthesis of the present invention in one embodiment is a self-expanding, fully supported and modular bifurcated system developed for endovascular repair of infrarenal abdominal aortic aneurysms (AAA). The main body of the graft consists of two parts, a distal bifurcated graft and a proximal tubular extension graft. The other components of the graft are the iliac legs which when coupled with the main bifurcated body provide a variety of overall device lengths. Ancillary devices such as body extenders, aorto-uni-iliac converters, and iliac plugs may also be required. Each individual device has it's own separate delivery system.

The bifurcated graft has one long limb with an iliac cuff and one short limb on the contra-lateral side.

There is a radiopaque marker at the graft bifurcation and a 'tick' marker at the distal end of the contra-lateral limb.

This bifurcated graft is pre-mounted into a deployment device with a tethered top stent introduction system which provides a controlled release for the graft. This graft is attached to the delivery system at both ends and released by three independent trigger wires. The first wire releases the compressed short leg, the second wire releases the proximal end of the graft and the third wire releases the distal end of the graft.

The proximal extension graft is a tubular structure with an exposed proximal attachment stent to allow for suprarenal fixation. Small radiopaque markers indicate the proximal edge of the graft.

This proximal extension graft is pre-mounted into a deployment device with a top cap introduction system which provides a controlled release for the graft. The exposed attachment stent is constrained within a top cap and held there by a trigger wire. The distal end of the graft is also attached to the delivery system and held by an independent wire.

The iliac legs are tubular grafts which are used to extend the composite graft into the iliac arteries. An iliac leg must be placed into the short limb from the contra-lateral side while a separate iliac leg can also be placed if needed into the long limb via the ipsilateral side.

Each component comes in a range of lengths and diameters which allows the physician to tailor the device to individual patient anatomies and to select the best iliac landing site. The diameter at the connecting end of both the proximal tubular extension graft and the distal bifurcated graft may be 22 or 24 mm. The diameter of the proximal end of the proximal tubular extension graft may be from 22 to 34 mm. The length of the proximal tubular extension graft may be from 73 to 131 mm. The diameter of the distal end of the a distal bifurcated graft may be from 12 to 24 mm. The length of the distal bifurcated graft to the bifurcation may be from 50 to 95 mm and the overall length may be from 100 to 180 mm. Spacing of the stents on the proximal extension graft may be from 1 to 8 mm. Spacing of the stents on the distal bifurcated graft may be from 0 to 1 mm on the body portion and from 1 to 3 mm on the longer leg portion.

Throughout this specification various indications have been given as to the scope of the invention but the invention is not limited to any one of these but may reside at two more of these combined together. The examples are given for illustration only and not for limitation.

Throughout this specification unless the context requires otherwise the words comprise and include and variations such as comprising and including will be understood to imply the inclusion of stated integers or group of integers but not the exclusion of any other integer or group of integers.

What is claimed is:

1. A composite prosthesis for deployment in a lumen, the prosthesis comprising a first substantially tubular prosthesis portion and a second substantially tubular prosthesis portion, wherein each prosthesis portion comprises a plurality of self expanding stents on an outer surface thereof along the length of each portion and at least one self expanding stent on an inside surface thereof at each end of each portion, each prosthesis portion comprising a connecting end to engage with the connecting end of the other prosthesis portion to form the composite prosthesis and a remote end at the opposite end to the connecting end, each connecting end comprising the same outside diameter as the other connecting end, whereby in use the connecting end of the first prosthesis portion can be deployed either inside or outside the connecting end of the second prosthesis portion with at least two stents overlapping and a smooth surface of one portion engaging with a smooth surface of the other portion to provide a seal therebetween.

2. A composite prosthesis as in claim 1, wherein the second prosthesis portion is a bifurcated graft including a body portion and two leg portions.

3. A composite prosthesis as in claim 2, wherein the bifurcated second prosthesis portion comprises a shorter leg and a longer leg and there are self expanding stents on the outside of the shorter leg and the inside of the remote end of the longer leg.

4. A composite prosthesis as in claim 2, further including at least one leg prosthesis portion to be deployed in use into either the longer or shorter legs of the bifurcated second prosthesis portion.

5. A composite prosthesis as in claim 1, wherein the first prosthesis portion comprises at its remote end a proximally extending self expanding stent including barbs to engage against the wall of a lumen.

6. A composite prosthesis comprising a first substantially tubular prosthesis portion and a second substantially tubular prosthesis portion, each prosthesis portion comprising a tubular body of a graft material and each including a connecting end, each connecting end comprising:
a terminal region providing a smooth external surface of the graft material with a stent or stents on the inside surface thereof; and
a second region adjacent to the terminal graft portion providing a smooth internal surface of the graft material with a stent or stents on the outside surface,
wherein the connecting end of the first prosthesis portion can be deployed inside the connecting end of the second prosthesis portion such that the smooth external surface of the terminal region of the first prosthesis portion engages the smooth internal surface of the second region of the second prosthesis portion to provide a seal therebetween or the connecting end of the second prosthesis portion can be deployed inside the connecting end of the first prosthesis portion such that the smooth external surface of the terminal region of the second prosthesis portion engages the smooth internal surface of the second region of the first prosthesis portion to provide a seal therebetween.

* * * * *